US00PP17197P2

(12) United States Plant Patent
White

(10) Patent No.: US PP17,197 P2
(45) Date of Patent: Nov. 7, 2006

(54) ***EPIMEDIUM* PLANT NAMED 'AMBER QUEEN'**

(50) Latin Name: *Epimedium wushanense×flavum*
Varietal Denomination: AMBER QUEEN

(76) Inventor: Anthony Robin White, Blackthorn Nursery Kilmeston Alresford, Hampshire SO24 ONL (GB)

( * ) Notice: Subject to any disclaimer, the term of this patent is extended or adjusted under 35 U.S.C. 154(b) by 0 days.

(21) Appl. No.: 11/190,344

(22) Filed: Jul. 26, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

Harris et al. Plant Identification Terminology an Illustrated Glossary 2$^{nd}$ ed. 2001, p. 23.*

* cited by examiner

*Primary Examiner*—Kent Bell
*Assistant Examiner*—June Hwu

(57) ABSTRACT

A new cultivar of *Epimedium* plant named 'AMBER QUEEN' that is characterized by clumping habit, spiny holly-like leaflets that are green and russet in color, and amber-orange spurred flowers that are held above two distinct layers of foliage. In combination these traits set 'AMBER QUEEN' apart from all other existing varieties of *Epimedium* known to the inventor.

3 Drawing Sheets

Genus: *Epimedium*. Species: *wushanense×flavum*. Denomination: 'AMBER QUEEN'.

BACKGROUND OF THE INVENTION

The present invention relates to a new and distinct cultivar of bishop's hat grown for use as an ornamental for container, rock garden, or as a groundcover in the landscape. The new cultivar is known botanically as *Epimedium wushanense×E. flavum* and will be referred to hereinafter by the cultivar name 'AMBER QUEEN'.

'AMBER QUEEN' is a plant hybrid that resulted from the deliberate cross-hybridization of *Epimedium wushanense* 'Caramel' (unpatented) and *Epimedium flavum* (unpatented). The seed parent is an individual *Epimedium wushanense* 'Caramel' and the pollen parent is an individual *Epimedium flavum*. The deliberate cross-hybridization was conducted in 1994 by the inventor at the inventor's nursery in Hampshire, England.

The inventor selected the new *Epimedium* cultivar named 'AMBER QUEEN' in 1994 based on the distinguishing characteristics of flower shape and flower color. The new *Epimedium* variety 'AMBER QUEEN' is readily distinguishable from the parents by flower shape and flower color. There are no close comparison plants known to the inventor.

'AMBER QUEEN' is semi-evergreen, characterized by clumping habit, spiny holly-like leaflets that are green and russet in color, and amber-orange spurred flowers that are held above the leaves. 'AMBER QUEEN' exhibits two distinct layers of foliage, due to the difference in length between basal stems and the subsequently basally branching stems. Essentially herbaceous, 'AMBER QUEEN' will retain leaves when winter temperatures are above minus 10° Centigrade.

The first asexual reproduction of the new *Epimedium* cultivar 'AMBER QUEEN' was conducted in 1995 by the method of division. Division of 'AMBER QUEEN' was accomplished by the inventor, at the inventor's nursery in Hampshire, England. Since that time the distinguishing characteristics of 'AMBER QUEEN' have been determined stable, fixed and reproduce true to type in successive generations.

SUMMARY OF THE INVENTION

The following traits have been repeatedly observed and represent the characteristics of the new *Epimedium* cultivar 'AMBER QUEEN'. These traits in combination distinguish 'AMBER QUEEN' from all other commercial varieties of *Epimedium* known to the inventor. 'AMBER QUEEN' has not been tested under all possible conditions and phenotypic differences may be observed with variations in environmental, climatic and cultural conditions, without however, any variance in genotype.

1. 'AMBER QUEEN' exhibits clumping habit.
2. The foliage of 'AMBER QUEEN' is semi-evergreen.
3. 'AMBER QUEEN' exhibits amber-orange spurred flowers that are held above two distinct layers of foliage.
4. 'AMBER QUEEN' exhibits spiny holly-like leaflets that are green with strong russet mottling when juvenile and green in color when mature.
5. 'AMBER QUEEN' is propagated by the method of division.
6. At maturity 'AMBER QUEEN' ranges from 60 cm. to 90 cm. in width, and ranges from 45 cm. to 75 cm. in height when in bloom.
7. Cultural requirements of 'AMBER QUEEN' are full deep shade to partial shade, fertile humus-rich soil, and regular water.
8. 'AMBER QUEEN' is hardy to minus 10° Centigrade and will retain leaves above this temperature.

9. 'AMBER QUEEN' is suitable for use in container, rock garden, or as a groundcover in the landscape.

11. 'AMBER QUEEN' blooms in April, May and June.

BRIEF DESCRIPTION OF THE DRAWINGS

The accompanying color drawings

Figure 1:
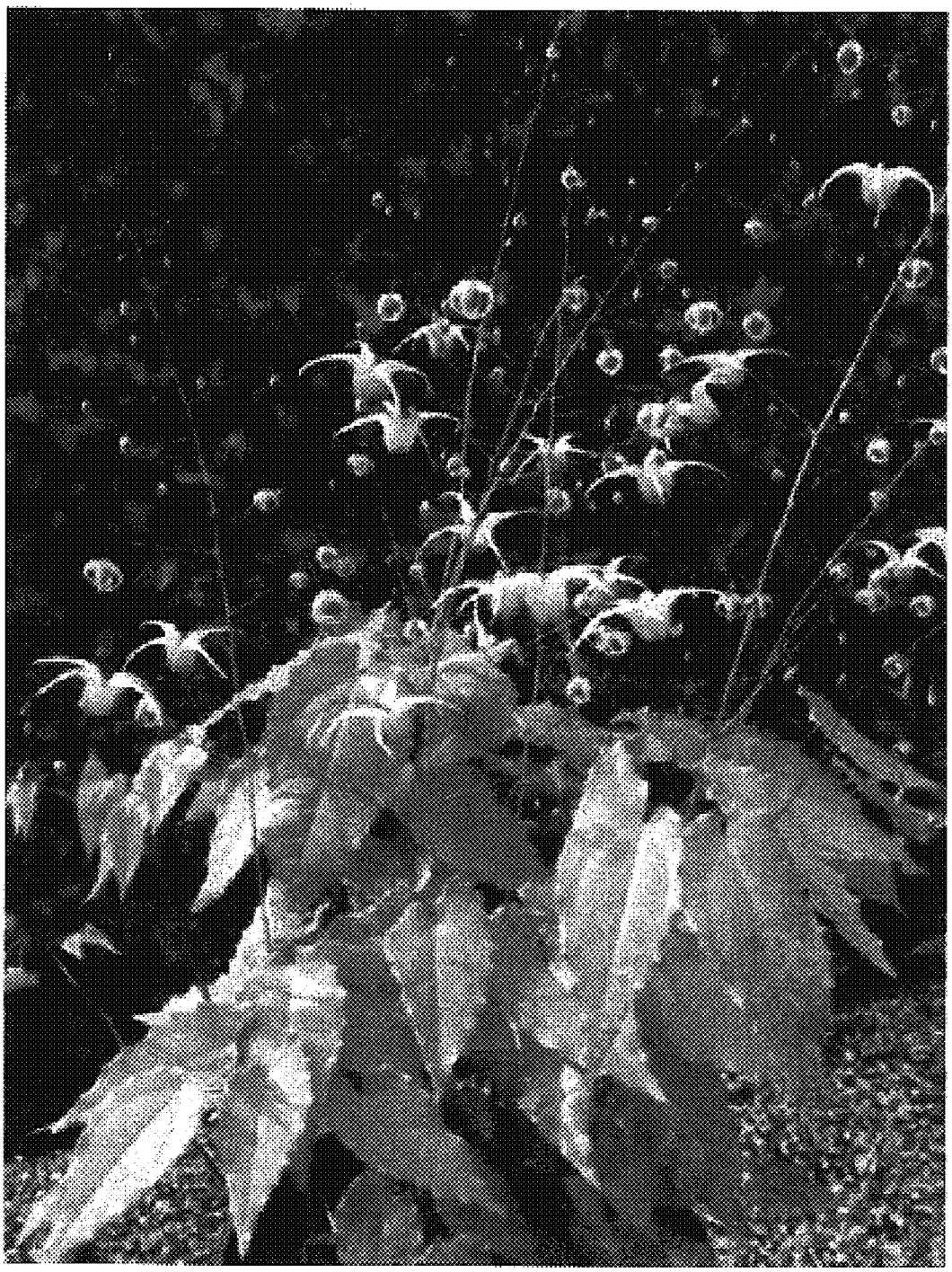
FIG. 1, FIG. 2 and FIG. 3 illustrate the overall appearance of the new *Epimedium* cultivar 'AMBER QUEEN' showing the colors as true as it is reasonably possible to obtain in colored reproductions of this type. The drawings were made in May and June 2005 from 12-month-old plants in 2-liter containers. The plants were greenhouse grown in Hampshire, England. Colors in the drawings may differ from the color values cited in the detailed botanical description, which accurately describe the actual colors of the new variety of *Epimedium* named 'AMBER QUEEN'.

The drawing labeled as FIG. 1 depicts a single whole plant of 'AMBER QUEEN' in flower.

Figure 2:
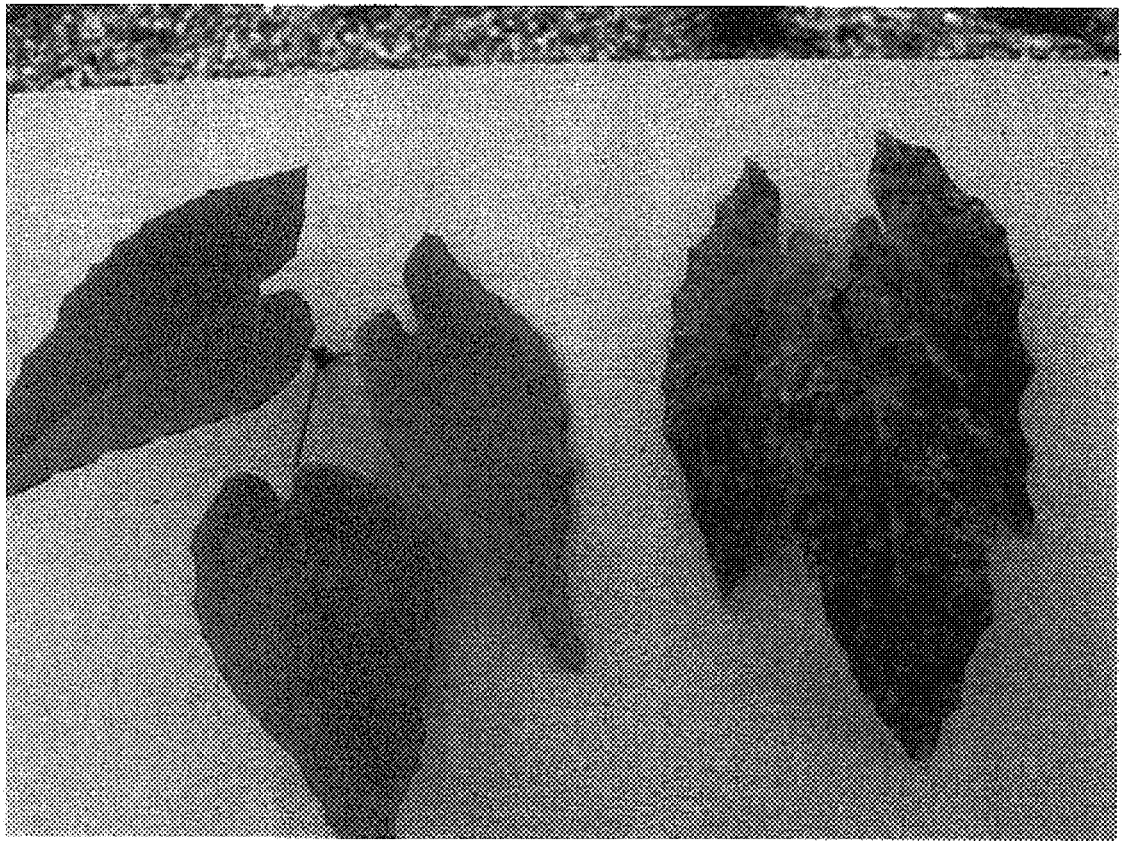

The drawing labeled as FIG. 2 depicts a close-up view of the mature and juvenile leaflets. The juvenile leaflets, shown on the right of the drawing, are initially strongly mottled with a reddish-brown colorations which disappear as spring advances. The leaflets, when mature, are shown on the left of the drawing, and are uniformly green in color.

Figure 3:
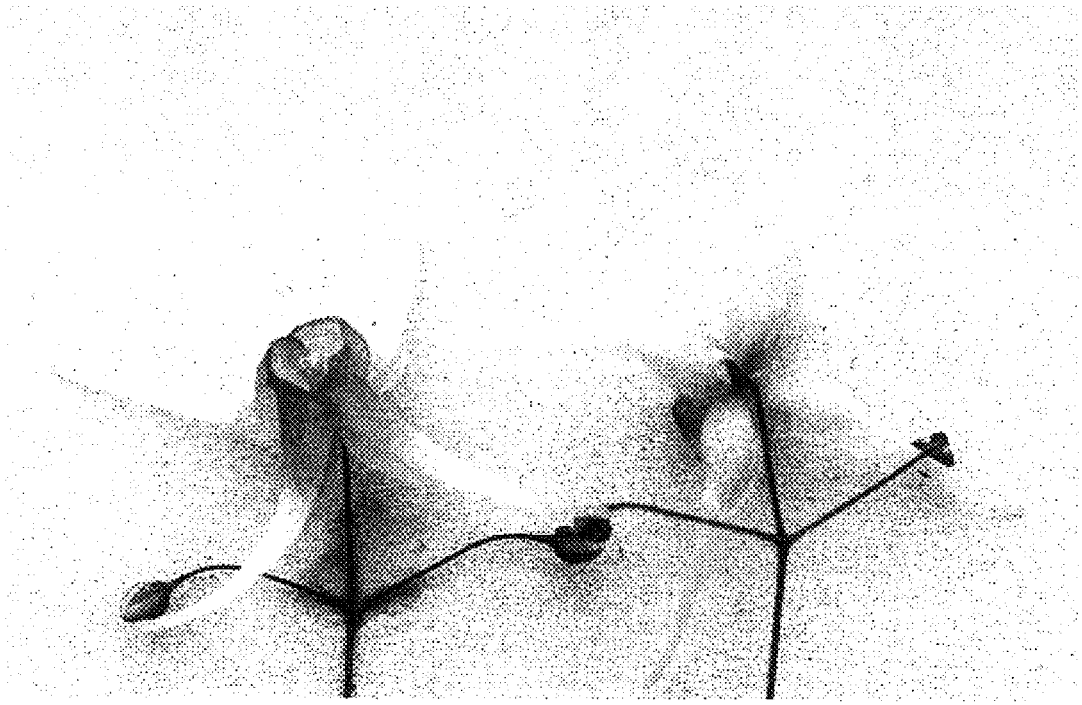

The drawing labeled as FIG. 3 depicts a close-up view of an inflorescence of 'AMBER QUEEN' which is suspended from the peduncle. The ventral aspect of the flower is downward facing and is shown on the left of the drawing with the flower rotated through 180 degrees. The dorsal aspect of the flower is shown on the right of the drawing.

FIG. 1, FIG. 2 and FIG. 3 were made using conventional techniques and although colors may appear different from actual colors due to light reflectance they are as accurate as possible by conventional photography.

BOTANICAL DESCRIPTION OF THE PLANT

The following is a detailed description of the new *Epimedium* variety named 'AMBER QUEEN'. Data was collected from 2-liter container plants that were greenhouse grown in Hampshire, England. The color determinations are in accordance with the 2001 edition of The Royal Horticultural Society Colour Chart, except where general color terms of ordinary dictionary significance are used. The growing requirements are similar to the species.

Botanical classification: *Epimedium wushanense*×*E. flavum* 'AMBER QUEEN'.

Genus: *Epimedium.*

Species: *wushanense*×*flavum.*

Denomination: 'AMBER QUEEN.'

Common name: Bishop's hat.

Commercial classification: Ornamental.

Plant type: Herbaceous perennial.

Commercial container size: Recommended commercial container size is a 2-liter container.

Cultural requirements: Provide full deep shade to partial shade, fertile humus-rich soil, and adequate but not excess water.

Plant parentage: 'AMBER QUEEN' is a plant hybrid that resulted from the deliberate cross-hybridization of the following parent plants:

*Seed parent.*—An individual *Epimedium wushanense* 'Caramel' (unpatented).

*Pollen parent.*—An individual *Epimedium flavum* (unpatented).

Plant description:

*Blooming period.*—April, May and June.

*Plant habit.*—Clumping habit.

*Plant use.*—Grown for use in container, rock garden or as a groundcover for the landscape.

*Vigor.*—Vigorous.

*Root system.*—Fine and fibrous roots.

*Plant width* (*at maturity*).—At maturity 'AMBER QUEEN' ranges from 60 cm. to 90 cm. in width.

*Plant height* (*at maturity*).—In bloom at maturity 'AMBER QUEEN' ranges from 45 cm. to 75 cm. in height.

*Plant growth rate.*—Plant spreads by rhizomes 1.5 cm. to 2.5 cm. annually.

*Plant hardiness.*—Hardy to minus 10° Centigrade.

*Plant propagation.*—Propagation is accomplished using the method of division.

*Crop time.*—12 months are needed to produce a commercial 2-liter container plant from division.

*Special growing considerations.*—Cut back in late winter before new growth resumes, and divide clumps in spring.

*Pest or disease resistance and susceptibility.*—No particular susceptibility or resistance to pests or diseases have been noted to date. In general, *Epimediums* are considered resistant to eating or browsing by deer but such has not yet been determined or confirmed for 'AMBER QUEEN'.

Stem:

*Branching habit.*—Basal stems arise from rhizomes with some branching at or around aerial emergence. All stems appear to arise from the base. The basally branching stems bear foliage at a height of 10 cm to 15 cm above the foliage of the basal (rhizomatous) stems.

*Stem color.*—152A.

*Stem dimensions.*—Range from 1 mm. to 3 mm. in diameter and 4 cm. to 30 cm. in length.

*Stem surface.*—Glaucous surface.

*Stem shape.*—Cylindrical.

*Stem texture.*—Wiry.

*Stem strength.*—Moderate.

*Stem pubescence.*—None observed.

*Rhizome color.*—Colors 185A, 185B, and 186D are individually present on an individual rhizome.

*Rhizome diameter.*—Rhizome is 2 mm. in diameter.

*Rhizome internode.*—Internode ranges from 1.5 cm. to 2 cm. in length.

Foliage:

*Foliage type.*—Semi-evergreen.

*Leaf arrangement.*—Whorled.

*Leaf division.*—Biternately compound leaf.

*Basal and cauline leaflet texture* (*juvenile leaflets*).—Satiny texture.

*Basal and cauline leaflet texture* (*mature leaflets*).—Leather-like texture.

*Durability of basal and cauline leaf to stress.*—Moderate to high durability.

*Basal and cauline leaflet margins* (*juvenile and mature*).—Serrate margins.

*Basal and cauline leaflet shape* (*juvenile and mature*).—Lanceolate shape.

*Basal and cauline leaflet apex* (*juvenile and mature*).—Acute apex.

*Basal and cauline leaflet base* (*juvenile and mature*).—Cordate base.
*Basal and cauline juvenile leaflet pubescence* (*abaxial and adaxial surfaces*).—None observed.
*Basal and cauline mature leaflet pubescence* (*abaxial and adaxial surfaces*).—None observed.
*Basal and cauline juvenile leaflet surface* (*abaxial surface*).—Glossy surface.
*Basal and cauline juvenile leaflet surface* (*adaxial surface*).—Glaucous surface.
*Basal and cauline mature leaflet surface* (*abaxial surface*).—Glossy surface.
*Basal and cauline mature leaflet surface* (*adaxial surface*).—Glaucous surface.
*Basal and cauline juvenile leaflet length.*—Leaflet is 6 cm. in length.
*Basal and cauline mature leaflet length.*—Leaflet is 8 cm. in length.
*Basal and cauline juvenile leaflet width.*—Leaflet is 3 cm. in width.
*Basal and cauline mature leaflet width.*—Leaflet is 3.5 cm. in width.
*Basal and cauline leaf and leaflet attachment.*—Petiolate attachment.
*Basal petiole dimensions.*—4 cm. to 5 cm. in length and 2.50 mm. in diameter.
*Cauline petiole dimensions.*—5.50 cm. in length and 2.50 mm. in diameter.
*Basal and cauline petiole color.*—152A.
*Basal petiolule dimensions.*—Petiolule is 1.50 mm. in diameter and 3 cm. to 5 cm. in length.
*Cauline petiolule dimensions.*—Petiolule is 1.50 mm. in diameter and 3 cm. to 5 cm. in length.
*Basal and cauline petiolule color.*—152A.
*Basal and cauline juvenile leaflet color* (*abaxial surface*).—146A.
*Basal and cauline juvenile leaflet color* (*adaxial surface*).—Opens russet brown 166A becoming green 138A or 138B with age, commencing at the base and along center vein and in spots or blotches which eventually coalesce to form entire green coloration in mature leaf.
*Basal and cauline mature leaflet color* (*abaxial surface*).—146A.
*Basil and cauline mature leaflet color* (*adaxial surface*).—138B.
*Basal and cauline venation pattern* (*juvenile and mature leaflets*).—Palmate.
*Basal and cauline juvenile leaflet vein color* (*abaxial surface*).—146A.
*Basal and cauline juvenile leaflet vein color* (*adaxial surface*).—166A except where replaced with 138A or 138B as leaflet matures.
*Basal and cauline mature leaflet vein color* (*abaxial surface*).—146A.
*Basal and cauline mature leaflet vein color* (*adaxial surface*).—138A.
*Fragrance.*—None observed.

Flower:
*Inflorescence type.*—Compound panicle.
*Number of flowers and buds.*—35–80 flowers and buds combined per individual 2-liter-container plant.
*Bloom period.*—April, May and June.
*Flower shape.*—Like a bishop's hat in shape.
*Flower diameter.*—Individual flowers range from 3 cm. to 3.5 cm. in diameter on an individual plant.
*Flower depth.*—Individual flowers are 1.75 cm. in depth.
*Flower color.*—Individual colors 165A, 170D, 8B, and 32A are present on an individual flower.
*Flower petals.*—Four petals in number.
*Petals fused or unfused.*—Petals are fused.
*Petal color* (*ventral and dorsal surfaces*).—32A.
*Petal dimensions* (*length*).—15 mm to 18 mm.
*Petal dimensions* (*width, depth, at base*).—Width 6 mm, depth 4.5 mm.
*Petal dimensions* (*width, depth, at 5 mm from base*).—Width 1.5 mm, depth 1.5 mm.
*Calcar* (*spur*).—Four in number.
*Calcar color.*—8B.
*Calcar dimensions.*—2 mm. in diameter and 1 cm. in length.
*Bud shape.*—Globular in shape.
*Bud surface.*—Pubescent.
*Bud apex.*—Obtuse apex.
*Bud color.*—Individual colors 165B and 175C are present on an individual bud.
*Bud dimensions.*—5 mm. in diameter and 5 mm. in height.
*Sepals.*—8 sepals in number per individual flower, 4 dorsal sepals and 4 ventral sepals. The 4 dorsal sepals are shed as an individual flower opens.
*Dorsal sepal surface* (*abaxial surface*).—Pubescent.
*Dorsal sepal surface* (*adaxial surface*).—Pubescent.
*Ventral sepal surface* (*abaxial surface*).—Pubescent.
*Ventral sepal surface* (*adaxial surface*).—Pubescent.
*Dorsal sepal shape.*—Narrowly ovate in shape.
*Ventral sepal shape.*—Narrowly ovate in shape.
*Dorsal sepal color.*—165A.
*Ventral sepal color.*—170D.
*Sepal margin* (*dorsal and ventral sepals*).—Entire.
*Sepal apex* (*dorsal and ventral sepals*).—Acuminate.
*Dorsal sepal length.*—Dorsal sepal ranges from 4 mm. to 5 mm. in length.
*Dorsal sepal width.*—2 mm. in width.
*Ventral sepal length.*—1 cm. in length.
*Ventral sepal width.*—4 mm. in width.
*Peduncle dimensions.*—Individual peduncle is 35 cm. in length and 2.50 mm. in diameter.
*Peduncle surface.*—Glaucous.
*Peduncle color.*—197B.
*Pedicel dimensions.*—Individual pedicel is 1.25 mm. in diameter and 2 cm. in length.
*Pedicel surface.*—Glaucous.
*Pedicel color.*—197B.
*Flower fragrance.*—None observed.

Reproductive organs:
*Stamens.*—4 stamens in number.
*Stamen color.*—9B.
*Pistil.*—One pistil in number.
*Pistil color.*—9B.
*Anther color.*—9B.
*Pollen color.*—9B.

Fruit:
*Fruit shape.*—Capsular.
*Fruit dimensions.*—1.5–2 cm. in length and 1.5 mm. in width.
*Fruit colors.*—Individual colors 146A and 144A are present on an individual fruit.

It is claimed:

1. A new and distinct cultivar of *Epimedium* plant named 'AMBER QUEEN', as described and illustrated herein.

* * * * *